US010086007B2

(12) United States Patent
Vidyasagar et al.

(10) Patent No.: US 10,086,007 B2
(45) Date of Patent: Oct. 2, 2018

(54) MATERIALS AND METHODS FOR TREATMENT OF CYSTIC FIBROSIS AND FOR INDUCTION OF ION SECRETION

(71) Applicant: University of Florida Research Foundation, Incorporated, Gainesville, FL (US)

(72) Inventors: Sadasivan Vidyasagar, Gainesville, FL (US); Paul Okunieff, Gainesville, FL (US); Sreekala Prabhakaran, Gainesville, FL (US); Lurong Zhang, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 0 days.

(21) Appl. No.: 14/390,301

(22) PCT Filed: Mar. 15, 2013

(86) PCT No.: PCT/US2013/031970

§ 371 (c)(1),
(2) Date: Oct. 2, 2014

(87) PCT Pub. No.: WO2013/151744

PCT Pub. Date: Oct. 10, 2013

(65) Prior Publication Data

US 2015/0044145 A1 Feb. 12, 2015

Related U.S. Application Data

(60) Provisional application No. 61/620,758, filed on Apr. 5, 2012, provisional application No. 61/637,675, filed on Apr. 24, 2012.

(51) Int. Cl.
*A61K 31/7004* (2006.01)
*A61K 9/00* (2006.01)
*A61K 38/16* (2006.01)

(52) U.S. Cl.
CPC ........ *A61K 31/7004* (2013.01); *A61K 9/0073* (2013.01); *A61K 38/162* (2013.01); *A61K 38/164* (2013.01)

(58) Field of Classification Search
None
See application file for complete search history.

(56) References Cited

U.S. PATENT DOCUMENTS 6,673,355 B1 1/2004 Estes

FOREIGN PATENT DOCUMENTS

WO WO 00/36915 * 6/2000 ............. A01N 37/30
WO WO 2012/020357 * 2/2012 ........... A61K 31/195

OTHER PUBLICATIONS

Castaneda, Francisco et al., "Thioglycosides as inhibitors of hSGLT1 and hSGLT2: Potential therapeutic agents for the control of hyperglycemia in diabetes," *International Journal of Medical Sciences*, 2007, 4(3):131-139.

(Continued)

*Primary Examiner* — Bethany P Barham
*Assistant Examiner* — Barbara S Frazier
(74) *Attorney, Agent, or Firm* — Saliwanchik, Lloyd & Eisenschenk

(57) ABSTRACT

The present invention provides materials and methods for inducing ion secretion and/or for treating cystic fibrosis. In one embodiment, the composition comprises glucose and/or a non-metabolizable glucose analog and/or non-structural protein (NSP4), a NSP4 peptide, or a NSP4 toxoid as the active ingredient, formulated with pharmaceutically-acceptable carriers. In a preferred embodiment, the composition is (Continued)

in a form of an aerosol preparation for intranasal and/or pulmonary administration, and is used to stimulate chloride and fluid secretion in nasal, tracheal and/or bronchial epithelium.

8 Claims, 9 Drawing Sheets

Specification includes a Sequence Listing.

(56) References Cited

OTHER PUBLICATIONS

Kunzelmann, Karl et al., "First Encounter: How Pathogens compromise Epithelial Transport," *Physiology*, 2004, 19:240-244.
Lorrot, Mathie et al., "How do the rotavirus NSP4 and bacterial enterotoxins lead differently to diarrhea," *Virology Journal*, 2007, 4:31.
Moriya, Ryuichi et al., "Activation of sodium-glucose cotransporter 1 ameliorates hyperglycemia by mediating incretin secretion in mice," *American Journal of Physiology Endocrinology & Metabolism*, 2009, 297:E1358-E1365.
Puntheeranurak, Theeraporn et al., "Substrate Specificity of Sugar Transport by Rabbit SGLT1: Single-Molecule Atomic Force Microscopy versus Transport Studies," *Biochemistry*, 2007, 46:2797-2804.

* cited by examiner

MATERIALS AND METHODS FOR TREATMENT OF CYSTIC FIBROSIS AND FOR INDUCTION OF ION SECRETION

CROSS-REFERENCE TO RELATED APPLICATIONS

This application is a National Stage Application of International Application Number PCT/US2013/031970, filed Mar. 15, 2013; which claims the priority benefit of U.S. Provisional Application Ser. No. 61/620,758, filed Apr. 5, 2012, and U.S. Provisional Application Ser. No. 61/637,675, filed Apr. 24, 2012, all of which are incorporated herein by reference in their entirety.

The Sequence Listing for this application is labeled "SeqList-14Mar13-ST25.txt", which was created on Mar. 14, 2013, and is 7 KB. The entire content is incorporated herein by reference in its entirety.

BACKGROUND OF INVENTION

Cystic fibrosis (CF) is a life-threatening, heritable disease that results from mutations in the cystic fibrosis transmembrane conductance regulator (CFTR) gene. The CFTR protein, which is located in the epithelium of various organs including the lungs, liver, pancreas, gastrointestinal tract, reproductive tract, and skin, is a cAMP-activated, ATP-gated ion channel that transports chloride and other ions across the epithelial cell membrane. In CF patients, defects in CFTR result in a reduction of chloride secretion, which in turn leads to a reduced fluid secretion due to solvent drag.

The hallmark symptoms of CF include the accumulation of thick, sticky mucus in various organs, particularly the lungs and pancreas. The presence of a thick mucus in the airways, including the lungs, nasal epithelium, and paranasal sinuses, results in impaired respiration, inflammation, and symptoms such as persistent coughing, wheezing, and shortness of breath. The thickened airway liquid also contributes to frequent infections and the development of diseases including pneumonia, bronchitis, and tuberculosis.

While management of CF has improved some over the years, options for treatment and care of CF patients remain limited. Specifically, there is a lack of effective means for inducing secretion in CF patients. As CF affects the lungs of most patients, a large part of the treatment routine involves clearing mucus from the airways, improving breathing, and preventing or ameliorating lung infection. Much of the treatment is accomplished through physical therapy.

Existing medications for improving respiratory function in CF patients include mucus-thinners, antibiotics, anti-inflammatory agents, and bronchodilators; furthermore, as lung function declines, lung transplantation might become necessary. There remains a need for development of additional and improved medicaments for CF. As will be clear from the following disclosures, these and other benefits are provided by the present invention.

BRIEF SUMMARY

The present invention provides materials and methods for increasing transport of chloride and/or other ions across the epithelial cell membrane, thereby inducing ion (e.g., anion) and/or fluid (e.g., water) secretion. In one embodiment, the present invention provides treatment for cystic fibrosis and diseases induced by cystic fibrosis. In a preferred embodiment, the present invention provides treatment for lung diseases induced by cystic fibrosis.

In one embodiment, the composition of the subject invention comprises glucose and/or a non-metabolizable glucose analog, and/or an isolated or substantially-pure non-structural protein (NSP4), a NSP4 peptide, or a toxoid of NSP4 as the active ingredient, formulated with one or more pharmaceutically-acceptable carriers.

In a preferred embodiment, the composition is in a form of an aerosol preparation for intranasal and/or pulmonary administration. In another embodiment, the present invention provides methods for treatment of cystic fibrosis and diseases induced by cystic fibrosis. In one embodiment, the method comprises administering, via an intranasal or pulmonary route, to a subject in need of such treatment, an effective amount of a composition of the invention.

Advantageously, in specific embodiments, the present invention stimulates chloride and fluid secretion in nasal, tracheal and/or bronchial epithelium, and thereby improves respiratory function of CF patients. In a preferred embodiment, the present invention provides treatment of lung diseases induced by cystic fibrosis.

BRIEF DESCRIPTION OF THE SEQUENCES

Figure 1:
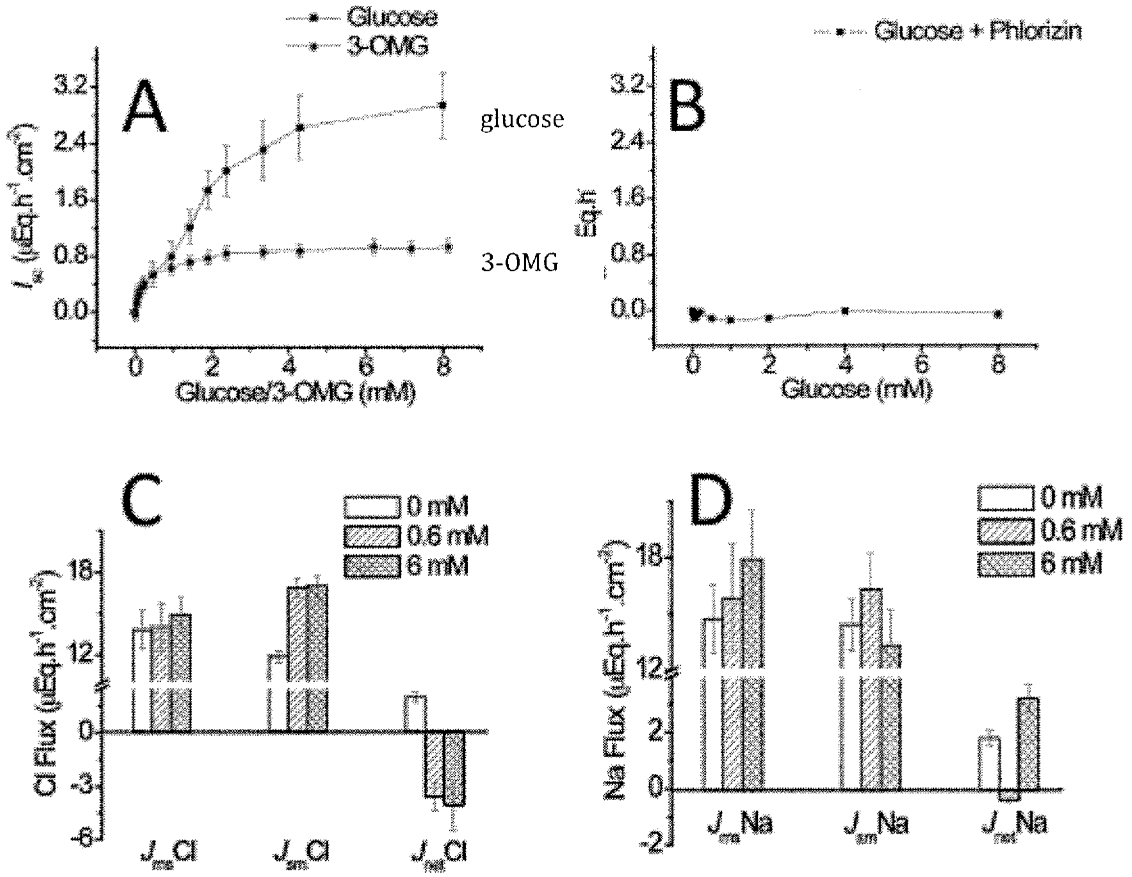
FIG. 1 shows that $Cl^-$ secretion contributes to the net glucose-stimulated increase in $I_{sc}$. Addition of increasing concentration of glucose or 3-O-methyl glucose (3-OMG) (A) to the lumen side shows dose-dependent increase in $I_{sc}$ with saturable kinetics. Nonlinear curve fit with the Michaelis-Menten model for enzyme kinetics for glucose results in $V_{max}$=3.3±0.19 μeq·h$^{-1}$·cm$^{-2}$ and $K_m$=0.24±0.06 mM (-■-). Addition of increasing lumen 3-OMG results in concentration-dependent increase in $I_{sc}$ with a $V_{max}$=1.9±0.13 μeq·h$^{-1}$·cm$^{-2}$ and $K_m$=0.22±0.07 mM (-●-). Addition of increasing concentration of glucose in tissues pre-treated with phlorizin shows no response to glucose (-■-) (B). The values are from n=6 tissues. Unidirectional and net flux of $Cl^-$ (C) shows no significant difference in $J_{ms}Cl^-$ at 0, 0.6 or 6 mM glucose. $J_{sm}Cl^-$ shows significant increase at 0.6 and 6 mM when compared to 0 mM glucose. 0 mM glucose shows significant $Cl^-$ absorption when compared to 0.6 mM and 6 mM glucose. (D) At 0 mM glucose there is net $Na^+$ absorption. $Na^+$ absorption is minimal at 0.6 mM but there is significant absorption at 6 mM glucose. Unidirectional fluxes ($J_{ms}$ and $J_{sm}$) do not show any significant difference at 0, 0.6 or 6 mM glucose). n=8 tissues

SEQ ID NO:1 is an amino acid sequence of a NSP4 protein useful according to the present invention.

SEQ ID NO:2 is an amino acid sequence of a NSP4 protein useful according to the present invention.

SEQ ID NO:3 is an amino acid sequence of a NSP4 protein useful according to the present invention.

SEQ ID NO:4 is an amino acid sequence of a NSP4 protein useful according to the present invention.

SEQ ID NO:5 is an amino acid sequence of a NSP4 114-135 peptide useful according to the present invention.

DETAILED DISCLOSURE

In one embodiment, the present invention provides materials and methods for treating cystic fibrosis. In a specific embodiment, the composition comprises glucose as the active ingredient, formulated with one or more pharmaceutically-acceptable carriers. In another embodiment, the composition comprises a non-metabolizable glucose analog as the active ingredient, formulated with one or more pharmaceutically-acceptable carriers. In another embodiment, the composition comprises, consists essentially of, or consists of, a substrate of sodium-glucose transporter (SGLT-1) and an isolated or substantially-pure NSP4 protein, peptide or toxoid as an active ingredient; and optionally, water, pharmaceutically acceptable carriers, and/or excipients.

In a preferred embodiment, the composition is in a form of an aerosol preparation for intranasal and/or pulmonary administration, and is used to stimulate chloride and fluid secretion in nasal, tracheal and/or bronchial epithelium.

In accordance with the present invention, experiments conducted using laser scanning laser microscopy show that glucose increases intracellular calcium levels in lung epithelial cells. The rise in intracellular calcium levels activates another chloride transport channel—calcium activated chloride channels (CaCCs). Patch clamp experiments show that glucose stimulates CaCC-mediated chloride secretion.

Induction of Ion Secretion by Glucose and NSP4

In accordance with the present invention, it has been found that lumen glucose induces net ion secretion in the small intestine. Specifically, glucose induces an active chloride secretion mediated by increased intracellular cAMP and $Ca^{2+}$ levels. Also, net $Na^+$ transport in the small intestine is absorptive at high glucose concentrations. In addition, glucose results in bicarbonate secretion in the small intestine.

Surprisingly, the present inventors have also found that the co-administration of glucose and NSP4 results in a significantly prolonged ion (such as chloride) and/or fluid secretion, which is markedly increased when compared to the level of ion (such as chloride) and/or fluid secretion induced by the administration of NSP4 alone. The results show that the co-administration of glucose and NSP4 produces a synergistic effect in inducing ion (such as chloride) and/or fluid secretion.

The present inventors have shown that an increase in intracellular cAMP level mediates $Cl^-$ and/or $HCO_3^-$ secretion. The $Cl^-$ and/or $HCO_3^-$ secretion is largely mediated by cystic fibrosis transmembrane conductance regulator (CFTR) ion channels, which have numerous (~20) potential serine and threonine phosphorylation sites. Protein kinase A (PKA) and protein kinase C (PKC) are known to activate CFTR anion channels. In patch clamp studies, it has been shown that CFTR channels are inactivated ("run down") quickly unless continuously activated by PKA, signifying the importance of PKA in the activation of CFTR. Consistent with this observation, pre-treatment of small intestine cells with a potent PKA inhibitor H89 results in a significant reduction in glucose-stimulated net increase in $I_{sc}$.

PKA antagonists have been shown to inhibit SGLT1 protein expression following glucose exposure (Dyer et al. (2003) *Eur. J. Biochem.* 270(16):3377-3388). CFTR channels are activated by the cAMP-dependent protein kinase (PKA), leading to anion secretion. Glucose-stimulated increase in $I_{sc}$ in the small intestine is partially mediated by CFTR-mediated ion transport.

Glucose as well as PKA agonists (such as cAMP) have been shown to increase the trafficking of SGLT1 to the brush border membrane (Wright et al. (1997) *J. Exp. Biol.* 200(Pt 2):287-293; Dyer et al. (2003) *Eur. J. Biochem.* 270(16): 3377-3388). The decrease in Vmax indicates a total decrease in current, which represents a decrease in glucose transport. The decrease in Vmax could result from a reduction of the total number of glucose transporter SGTL1, which is mostly found in villus epithelial cells. The loss of villus results in a significant loss of available transporter for taking glucose into the cells.

It has been found that incubating enterocytes with glucose increases intracellular cAMP levels. A greater increase in glucose-induced intracellular cAMP level is observed in villus cells than in crypt cells. Incubating enterocytes with forskolin increases intracellular cAMP levels in both crypt and villus cells. SGLT1-mediated glucose transport occurs primarily in villus cells instead of in crypt cells, as a greater number of SGLT-1 are located in the villus region than in the crypt region (Knickelbein et al. (1988) *J. Clin. Invest.* 82(6):2158-2163). Accordingly, increasing glucose concentrations in crypt cells does not result in increased cAMP response.

Even at low concentration (e.g., 0.6 mM glucose that is approximately half of its $V_{max}$), lumen glucose induces net anion secretion. At higher concentrations of glucose, sodium absorption is predominant. Increased lumen glucose concentration increases intracellular cAMP and $Ca^{2+}$ levels. Previous studies have shown that $K_m$ for $Na^+$-coupled glucose transport is in a range of 0.2 to 0.7 mM (Lo & Silverman (1998) *J. Biol. Chem.* 273 (45):29341-29351).

The presence of a residual glucose-mediated increase in Isc in cells pre-treated with H-89 indicates that PKA independent pathway(s) exist in glucose-induced anion secretion. Electrogenic anion secretion across the small intestine is mediated by ion channels, which can be classified based on their mechanisms of activation, such as activation by cAMP, $Ca^{2+}$, cell-volume and membrane potential.

It has also been found that lumen glucose induces an increase in intracellular $Ca^{2+}$ levels. Also, the glucose-induced $Cl^-$ secretion is mediated by PKA-dependent as well as PKA-independent pathways. This indicates that, in addition to CFTR, calcium activated chloride channels (CaCCs) also play a role in glucose-induced anion secretion.

In addition, glucose stimulates electrogenic $HCO_3^-$ secretion. Small intestine cells incubated with glucose exhibit higher levels of $HCO_3^-$ secretion in lumen CF-containing solution than in lumen CF free solution. These results indicate that anion channels mediate $HCO_3^-$ secretion in the presence of glucose. Also, addition of glucose results in a slight decrease in $Cl^-$—$HCO_3^-$ exchange, when compared to cells with no glucose addition. This decrease may be secondary to an increase in intracellular cAMP level with glucose. This also indicates that glucose induces anion channel-mediated secretion and inhibits electroneutral $Cl^-$—$HCO_3^-$ exchange.

In addition, small intestine cells were incubated with an anion channel blocker (100 mM NPPB) and an anion exchange inhibitor (100 mM DIDS), respectively. There was significant inhibition of glucose-induced, anion channel-mediated $HCO_3^-$ secretion by NPPB (100 mM) (4.2±0.7 vs 7.6±1.5 $mEq \cdot h^{-1} \cdot cm^{-2}$).

In the presence of anion channel inhibitors, residual $HCO_3^-$ secretion is still observed. This indicates that $Cl^-$—$HCO_3^-$ exchange is present in glucose-mediated secretion. This also indicates that an elevated intracellular calcium level could inhibit sodium-hydrogen exchanger 3 (NHE3) activity during normal digestive function as well as in certain disease conditions. This also indicates that SGLT1 plays a dual role in regulating sodium absorption and some times, stimulating a secretory and/or an absorptive defect.

The discovery of glucose-induced secretory mechanism can be used in the treatment of gastrointestinal diseases including diarrhea. Patients with acute diarrheal diseases commonly have impaired glucose absorption that occurs in the upper gastrointestinal tract. The presence of unabsorbed carbohydrates can exert an osmotic effect in the bowel, leading to diarrhea. In addition, glucose increases intracellular $Ca^{2+}$ and/or cAMP levels and induces anion secretion. The secretory effects of glucose have been previously understudied or masked by concurrent $Na^+$-glucose absorption. Also, due to its secretory effects, glucose administration particularly exacerbates gastrointestinal diseases with impaired $Na^+$-glucose absorption, such as Crohn's disease and irradiation or chemotherapy-induced enteritis that are associated with shortening of the villi and, therefore, extremely compromised absorption.

Therapeutic Compositions

In one aspect, the present invention provides therapeutic compositions for increasing transport of chloride and/or other ions across the epithelial cell membrane, thereby inducing increased ion (e.g., anion) and/or fluid (e.g., water) secretion. In one embodiment, the composition induces chloride and/or fluid (e.g., water) secretion. In one embodiment, the composition of the present invention can be used to treat cystic fibrosis and diseases induced by cystic fibrosis including, lung diseases induced by cystic fibrosis.

In a preferred embodiment, the composition is formulated in a form of an aerosol preparation for intranasal and/or pulmonary administration.

In one embodiment, the composition comprises glucose as the active ingredient, formulated with one or more pharmaceutically-acceptable carriers.

In one embodiment, the composition comprises, consists essentially of, or consists of, a substrate of sodium-glucose transporter (SGLT-1) as the active ingredient; and optionally, water, pharmaceutically acceptable carriers, excipients, buffering agents, dispersing agents, bulking agents, surfactants, diluents, colorants, and/or preservatives.

Representative examples of SGLT-1 substrates useful according to the present invention include, but are not limited to, glucose, non-metabolizable glucose analogs such as α-methyl-D-glucopyranoside (AMG), 3-O-methylglucose (3-OMG), deoxy-D-glucose, and α-methyl-D-glucose. Substrates of SGLT-1 can be selected based on agonist assays known in the art. Also, structural modifications of glucose and other carbohydrates (such as sugars) can be made to obtain substrates of SGLT-1.

In one embodiment, the composition comprises, consists essentially of, or consists of glucose as the active ingredient; and optionally, water, and one or more pharmaceutically acceptable carriers, excipients, buffering agents, dispersing agents, bulking agents, surfactants, diluents, colorants, and/or preservatives.

In another embodiment, the composition comprises, consists essentially of, or consists of, a non-metabolizable glucose analog (e.g., α-methyl-D-glucopyranoside (AMG), 3-O-methylglucose (3-OMG), and α-methyl-D-glucose) as the active ingredient; and optionally, water, and one or more pharmaceutically acceptable carriers, excipients, buffering agents, dispersing agents, bulking agents, surfactants, diluents, colorants, and/or preservatives.

In one embodiment, the composition comprises a SGLT-1 substrate (e.g., glucose, a non-metabolizable glucose analog) at a concentration of 2 mM or lower including, but not limited to, 2, 1.5, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.008, 0.005, 0.003, 0.001, 0.0005, 0.0003, 0.0001, $10^{-5}$, $10^{-6}$, $10^{-7}$, $10^{-8}$ or $10^{-9}$ mM.

In certain embodiments, the composition comprises a SGLT-1 substrate (e.g., glucose, a non-metabolizable glucose analog) at a concentration of 0.3 mM to 3.0 mM, or any value therebetween including, but not limited to, 0.5 mM to 1.5 mM, and 0.8 mM to 1.2 mM.

In another embodiment, the composition comprises, consists essentially of, or consists of, an isolated or substantially-pure non-structural protein (NSP4), a NSP4 peptide, or a toxoid of NSP4 as the active ingredient; and optionally, water, pharmaceutically acceptable carriers, excipients, buffering agents, dispersing agents, bulking agents, surfactants, diluents, colorants, and/or preservatives.

In another embodiment, the composition comprises, consists essentially of, or consists of, nucleic acid molecules encoding non-structural protein (NSP4), a NSP4 peptide, or a toxoid of NSP4 as the active ingredient.

The non-structural protein NSP4 is an entero-toxin produced by rotavirus. The NSP4 proteins, peptides and toxoids useful according to the present invention include, but are not limited to, a protein comprising the entire amino acid sequence of NSP4, non-glycosylated NSP4, and fragments of the NSP4 protein including, but not limited to, the NSP4 peptide fragments comprising amino acids 112-175 of the NSP4 protein and any peptide fragments of NSP4 112-175 including, but not limited to, the NSP4 114-135 peptide, the NSP4 116-135 peptide, the NSP4 118-135 peptide, the NSP4 118-133 peptide, the NSP4 120-130 peptide, and the NSP4 112-150 peptide.

The amino acid sequences of the NSP4 proteins, peptides and toxoids useful according to the present invention can be derived from all publically-available NSP4 sequences, which can be accessed, for example, via the GenBank database and databases containing published patents and patent applications. Non-limiting examples of NSP4 proteins include, but are not limited to, human rotavirus NSP4 (GenBank Accession No. BAE72460.1; SEQ ID NO:1), GenBank Accession No. AAC61867 (SEQ ID NO:2), GenBank Accession No. AAB58700 (SEQ ID. NO:3), and GenBank Accession No. BAA13728 (SEQ ID NO:4).

In a specific embodiment, the amino acid sequence of NSP4 114-135 peptide is SEQ ID NO:5. In one embodiment, the NSP4 peptide comprises SEQ ID NO:5; a fragment having more than 5, 6, 7, 8, 9, 10, 11, 12, 13, 14, 15, 16, 17, 18, 19, 20, or 21 consecutive amino acids of SEQ ID NO:5; an amino acid sequence having modifications (e.g., insertion, deletion, substitution) of no more than 1, 2, 3, 4, 5, 6, or 7 amino acid of SEQ ID NO:5, or a fragment thereof; or an amino acid sequence having at least 80% identity (such as, at least 85%, 90%, 93%, 95% identity) to SEQ ID NO:5.

In certain embodiments, the composition comprises NSP4 proteins, peptides (such as NSP4 114-135) and toxoids at a concentration of 0.2 μM to 20 μM, or any value therebetween including, but not limited to, 0.2 μM to 15 μM, 2.0 μM to 15 μM, and 2.0 μM to 10 μM. In certain embodiments, NSP4 proteins, peptides and toxoids useful according to the present invention comprise amino acid modifications of the naturally-occurring or publically-available NSP4 sequences, for providing similar or improved therapeutic effects. Examples of amino acid modifications include, but are not limited to, insertions, deletions, substitutions, and chemical modifications of one or more amino acids.

Amino acids can be generally categorized in the following classes: non-polar, uncharged polar, basic, and acidic. In one embodiment, amino acids of a naturally-occurring or publically-available NSP4 sequence can be replaced with another natural or non-natural amino acid of the same class and fall within the scope of the present invention so long as the modified NSP4 protein, peptide, or toxoid having the substitution still retains substantially the same functional activity (e.g., induction of ion (such as chloride) and/or fluid secretion) as the NSP4 protein, peptide, or toxoid that does not have the substitution. Polynucleotides encoding a modified fusion protein having one or more amino acid substitutions in the sequence are also within the scope of the present invention. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The proteins, peptides, and toxoids useful according to the present invention can be isolated from rotavirus, can be chemically synthesized, or can be recombinantly produced. Methods of isolation, synthesis, and recombinant production of NSP4 proteins, peptides, and toxoids are known in the art. In one embodiment, the NSP4 proteins, peptides, and toxoids can be produced from expression vectors including, but not limited to, mammalian, yeast, bacterial, and insect expression vectors.

In one further embodiment, the composition comprises, consists essentially of, or consists of, a substrate of sodium-glucose transporter (SGLT-1) and an isolated or substantially-pure NSP4 protein, peptide or toxoid as the active ingredient; and optionally, water, pharmaceutically acceptable carriers, and/or excipients.

In one embodiment, the composition is formulated such that, when administered to a cell or a subject, the NSP4 protein, peptide or toxoid is not released until the SGLT-1 substrate (e.g., glucose or non-metabolizable glucose analogs such as AMG, 3-OMG, etc) is released. In one embodiment, the composition is formulated such that, when administered to a cell or a subject, the SGLT-1 substrate is released before the release of the NSP4 protein, peptide or toxoid. In one embodiment, the composition is formulated such that, when administered to a cell or a subject, the SGLT-1 substrate is released simultaneously with the NSP4 protein, peptide or toxoid.

In one specific embodiment, the NSP4 protein, peptide or toxoid is contained or encapsulated within a structure (such as a coating, scaffold, matrix) that comprises, or is made of materials comprising a SGLT-1 substrate. In another specific embodiment, the NSP4 protein, peptide or toxoid is contained in one structure and the SGLT-1 substrate is contained in another structure, and during administration, the NSP4 protein, peptide or toxoid is not released until the SGLT-1 substrate is released.

In one embodiment, the composition is formulated for oral administration.

In another embodiment, the composition is formulated as an aerosol preparation for intranasal and/or pulmonary administration. In a specifically preferred embodiment, the composition is a nasal spray. In a preferred embodiment, the nasal spray preparation is formulated as a mist of liquid, saline formulation.

The term "aerosol," as used herein, refers to its ordinary meaning in pharmacology that is a type of drug preparation administered by inhalation through the nose or mouth. An aerosol is a suspension or dispersion of finely-divided solid or liquid particles in air or other gaseous environment. Aerosol formulations are particularly useful for treating respiratory disorders because they can deliver drugs directly to the site of action and thereby minimize the risk of systemic side effects. In some embodiments of the subject invention, aerosol devices contain drugs dispersed in a pressurized gas, and are designed to deliver a precise dose each time. Nasal sprays, an embodiment of the aerosol preparation, can be used either to deliver drugs on the nasal mucosa or to deliver drugs that are absorbed through the mucosa and exert an effect on another organ.

In one embodiment, the aerosol formulation of the present invention is prepared as a dry powder formulation comprising a finely-divided dry powder form of the active ingredient(s) and, optionally, a dispersant. In certain embodiments, the dry powder form of the aerosol can have a particle size ranging from 1 to 1000 μm, or any size therebetween including, but not limited to, 10 to 700 μm, 20 to 500 μm, 30 to 250 μm, 40 to 150 μm, or 50 to 100 μm.

In another embodiment, the aerosol formulation of the present invention is prepared as a mist comprising a liquid form of the active ingredient(s) and, optionally, a dispersant. In certain embodiments, the liquid form of aerosol can have a droplet (particle) size ranging from 1 to 1000 μm, or any size therebetween including, but not limited to, 10 to 700 μm, 20 to 500 μm, 30 to 250 μm, 40 to 150 μm, or 50 to 100 μm.

In one embodiment, at least one component of the composition is formulated as a sustained-release formulation.

The term "consisting essentially of," as used herein, limits the scope of the ingredients and steps to the specified materials or steps and those that do not materially affect the basic and novel characteristic(s) of the present invention, e.g., compositions and methods for treatment of cystic fibrosis, for activation of SGLT-1, for inducing ion (e.g., chloride) and/or fluid secretion, and/or for activation of CaCCs (e.g., TMEM16a). For instance, "consisting essentially of," means that the therapeutic composition does not contain any unspecified ingredients including, but not limited to, unspecified free amino acids; di-, oligo-, or polypeptides; proteins; mono-, di-, oligo-, polysaccharides; carbohydrates; fatty acids; and lipids that have a direct beneficial or adverse therapeutic effect on the treatment of cystic fibrosis, activation of SGLT-1, induction of ion (e.g., chloride) and/or fluid secretion, and/or activation of CaCCs (e.g., TMEM16a). Also, use of the term "consisting essentially of," indicates that the composition may comprise substances that do not have therapeutic effects on treatment of cystic fibrosis, activation of SGLT-1, induction of ion (e.g., chloride) and/or fluid secretion, and/or activation of CaCCs (e.g., TMEM16a); such ingredients include carriers, excipients, buffering agents, dispersing agents, bulking agents, surfactants, diluents, colorants, and preservatives, that do not affect treatment of cystic fibrosis, activation of SGLT-1, induction of ion (e.g., chloride) and/or fluid secretion, and/or activation of CaCCs (e.g., TMEM16a).

In a further embodiment, the composition does not contain one or more ingredients selected from di-, oligo-, or polysaccharides; carbohydrates; free amino acids; di-, oligo-, or polypeptides; proteins; nucleic acids; small-, medium-, and/or long-chain fatty acids; lipids; acid or vitamins.

The term "oligopeptide," as used herein, refers to a peptide consisting of three to twenty amino acids. The term "oligosaccharides," as used herein, refers to a saccharide consisting of three to twenty monosaccharides.

In one embodiment, the total osmolarity of the composition is from about 230 mosm to 280 mosm, or any value therebetween. In certain embodiments, the total osmolarity is from about 250 to 260 mosm. In another embodiment, the composition has a total osmolarity that is any value lower than 280 mosm.

In certain preferred embodiments, the total osmolarity of the composition is from 230 mosm to 390 mosm, or any value therebetween including, but not limited to, 275 mosm to 340 mosm, 280 mosm to 320 mosm, and 290 mosm to 310 mosm In one embodiment, the composition is slightly alkaline. In certain embodiments, the composition has a pH from about 7.1 to 7.9, or any value therebetween. In certain embodiments, the composition has a pH from about 7.3 to 7.5, about 7.2 to 7.4, or about 7.2.

In certain embodiments, the composition has a pH from about 5.0 to 7.5 or any value therebetween including, but not limited to, 5.5 to 7.2, 5.5 to 6.9, and 5.7 to 6.5.

Induction of Ion Secretion and Treatment of Cystic Fibrosis

Another aspect of the present invention provides methods for increasing transport of chloride and/or other ions across the epithelial cell membrane, thereby inducing ion (e.g., anion) and/or fluid (e.g., water) secretion. The present invention also provides treatment for diseases in which increased transport of chloride and/or other ions across the epithelial cell membrane, and/or increased ion (e.g., anion) and/or fluid secretion is beneficial.

In one embodiment, the present invention induces chloride and/or fluid secretion, and can be used in the treatment of diseases in which increased chloride and/or fluid secretion is beneficial. Advantageously, the present invention can produce sustained chloride and/or fluid secretion for a prolonged period of time (e.g., 1 hour, 2 hours, 3 hours, 4 hours, 5, hours, 6 hours, 12 hours, 18 hours, 24 hours, or 48 hours) after the administration of the composition at each time.

In one embodiment, the present invention provides a method of inducing ion (e.g., chloride and other anions) and/or fluid (e.g., water) secretion from cells, comprising administering to a cell in need of such induction, a composition of the invention. In one embodiment, the composition of the present invention is administered to an epithelial cell. In one specific embodiment, the composition of the present invention is administered to cells in an animal subject.

In one embodiment, the present invention provides methods for treatment of cystic fibrosis. In preferred embodiments, the present invention, via intranasal and/or pulmonary administration of the composition, stimulates chloride and fluid secretion in nasal, tracheal and/or bronchial epithelium of CF patients. In a preferred embodiment, the present invention provides methods for treatment of cystic fibrosis-induced lung diseases.

In one embodiment, the method comprises administering, to a subject in need of such treatment, an effective amount of a composition of the invention.

In one embodiment, the present invention provides a method of increasing ion (e.g., chloride) and/or fluid secretion in a cell, wherein the method comprises administering, to said cell in need of such induction, an effective amount of a composition comprising, consisting essentially of, or consisting of, a substrate of sodium-glucose transporter (SGLT-1) (e.g., glucose or non-metabolizable glucose analogs such as AMG, 3-OMG, etc) as the active ingredient; and optionally, water, pharmaceutically acceptable carriers, excipients, buffering agents, dispersing agents, bulking agents, surfactants, diluents, colorants, and/or preservatives.

In one embodiment, the present invention provides a method of increasing ion (e.g., chloride) and/or fluid secretion in a cell, wherein the method comprises administering, to said cell in need of such induction, an effective amount of a composition comprising, consisting essentially of, or consisting of, an isolated or substantially-pure NSP4 protein, peptide or toxoid as the active ingredient; and optionally, water, pharmaceutically acceptable carriers, and/or excipients.

In another embodiment, the present invention provides a method of increasing ion (e.g., chloride) and/or fluid secretion in a cell, wherein the method comprises administering, to said cell in need of such induction, an effective amount of a composition comprising, consisting essentially of, or consisting of, a substrate of sodium-glucose transporter (SGLT-1) and an isolated or substantially-pure NSP4 protein, peptide or toxoid as the active ingredient; and optionally, water, pharmaceutically acceptable carriers, and/or excipients.

Cells to which the composition of the present invention can be administered include, but are not limited to, cells of the lungs, nasal epithelium, paranasal sinuses, liver, pancreas, gastrointestinal tract, reproductive tract, and skin. In one embodiment, the cell to which the composition of the present invention is administered is a cell of a subject.

In another specific embodiment, the present invention provides a method of treating cystic fibrosis, wherein the method comprises administering, to a subject in need of such treatment, an effective amount of a composition comprising, consisting essentially of, or consisting of, a substrate of sodium-glucose transporter (SGLT-1) (e.g., glucose or non-metabolizable glucose analogs such as AMG, 3-OMG, etc) as the active ingredient; and optionally, water, pharmaceutically acceptable carriers, excipients, buffering agents, dispersing agents, bulking agents, surfactants, diluents, colorants, and/or preservatives.

In another specific embodiment, the present invention provides a method of treating cystic fibrosis, wherein the method comprises administering, to a subject in need of such treatment, an effective amount of a composition comprising, consisting essentially of, or consisting of, an isolated or substantially-pure NSP4 protein, peptide or toxoid as the active ingredient; and optionally, water, pharmaceutically acceptable carriers, and/or excipients.

In another specific embodiment, the present invention provides a method of treating cystic fibrosis, wherein the method comprises administering, to a subject in need of such treatment, an effective amount of a composition comprising, consisting essentially of, or consisting of, a substrate of sodium-glucose transporter (SGLT-1) and an isolated or substantially-pure NSP4 protein, peptide or toxoid as the active ingredient; and optionally, water, pharmaceutically acceptable carriers, and/or excipients.

In practicing the treatment methods of the present invention, the NSP4 protein, peptide or toxoid can be administered before, during, or after the administration of the SGLT-1 substrate. In one specific embodiment, the SGLT-1 substrate is administered before the administration of the SGLT-1 substrate. In another specific embodiment, the SGLT-1 substrate is administered simultaneously with the NSP4 protein, peptide or toxoid.

In preferred embodiments, the composition is administered via intranasal or pulmonary delivery. In another embodiment, the composition is administered orally.

The term "treatment" or any grammatical variation thereof (e.g., treat, treating, and treatment etc.), as used herein, includes but is not limited to, alleviating or ameliorating a symptom of a disease or condition; and/or reducing the severity of a disease or condition.

In certain embodiments, treatment includes one or more of the following: alleviating or ameliorating cystic fibrosis; stimulating chloride and/or fluid secretion in organs including the lungs, nasal epithelium, paranasal sinuses, liver, pancreas, gastrointestinal tract, reproductive tract, and skin; alleviating or reducing the accumulation or thickening of mucus in organs including the airways (including the lungs, nasal epithelium, and paranasal sinuses), liver, pancreas, gastrointestinal tract, reproductive tract, and skin; improving lung function; and improving respiratory function such as improving ease of breaching and reducing coughing.

The term "effective amount," as used herein, refers to an amount that is capable of treating or ameliorating a disease or condition or otherwise capable of producing an intended therapeutic effect.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, cats; live stocks such as horses, cattle, pigs, sheep, goats, chickens; and other animals such as mice, rats, guinea pigs, and hamsters.

In one embodiment, the cell or the subject in need of treatment has functional glucose transport proteins, such as, SGLT-1 proteins. In another embodiment, the cell or the subject in need of treatment has functional calcium ($Ca^{2+}$)-activated chloride proteins, such as transmembrane protein 16a (TMEM16a). In another embodiment, the cell or the subject in need of treatment does not have, or has defective, CFTR proteins.

In one embodiment, the subject in need of treatment has, or is diagnosed with, cystic fibrosis. Cystic fibrosis can be diagnosed at birth through newborn screening. Common tests for diagnosis of cystic fibrosis include sweat test and genetic testing.

In one embodiment, the subject in need of treatment has, or is diagnosed with, cystic fibrosis-induced lung diseases.

In one embodiment, the human subject is a child of less than fourteen years old, or of any age younger than nine years old, such as five years old, three years old, two years old, or one year old. In another embodiment, the human subject in an infant of less than one year old, or any age younger such as less than nine, six, or three months old.

In one embodiment, the subject in need of treatment has mutations in CFTR genes, and thereby has reduced chloride and/or fluid secretion when compared to a control normal subject. CF is an autosomal recessive disease. While a subject that has a functional copy and a non-functional copy of the CFTR gene may not be characterized as having CF, such subject would benefit from, and thus, (in one embodiment of the invention) is considered as in need of the treatment of the invention.

In one embodiment, the present invention can be used to treat diseases and conditions with reduced chloride and/or fluid secretion in epithelial cells of various organs including, but not limited to, the lungs, nasal epithelium, and paranasal sinuses, liver, pancreas, gastrointestinal tract, reproductive tract, and skin. In another embodiment, the present invention can be used to treat diseases and conditions that would benefit from increased CaCC (e.g., TMEM16a)-activated chloride and/or fluid secretion. In one embodiment, the present invention can be used to stimulate chloride and/or fluid secretion in nasal, tracheal and/or bronchial epithelium of CF patients. In one embodiment, the present invention is used to clear dry inspissated mucous in cystic fibrosis patients and/or in dry and atrophic nasal mucosa.

In one embodiment, the present invention is used to treat lung diseases induced by cystic fibrosis. In one embodiment, the present invention can be used to treat diseases and conditions induced by cystic fibrosis including, but not limited to, respiratory diseases including, but not limited to, inflammation in the airways (including the lungs, and paranasal sinuses), bronchiectasis, pulmonary hypertension, pneumonia, bronchitis, tuberculosis, pulmonary and/or airway infection by pathogens including, but not limited to, *Staphylococcus aureus, Haemophilus influenzae, Pseudomonas aeruginosa*, and *Mycobacterium avium*; CF-related diseases and conditions in the pancreas, liver, intestine and other organs of the gastrointestinal tract; endocrine diseases such as CF-related diabetes; infertility; and CF-related skin diseases and conditions such as salty-tasting skin.

In one embodiment, the compositions of the present invention are delivered into the airways, including the lungs, and paranasal sinuses. In one embodiment, the present invention is used to induce ion (e.g., chloride) and/or secretion in the gastrointestinal tract, such as for example, the small intestine.

Formulations and Delivery Systems

The present invention also provides therapeutic or pharmaceutical compositions comprising the active ingredient in a form that can be combined with a therapeutically or pharmaceutically acceptable carrier. In a preferred embodiment, the composition is in a form of an aerosol preparation for intranasal and/or pulmonary administration. In another embodiment, the composition is formulated for oral administration.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

Conventional pharmaceutical excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like, can be used in accordance with the present invention. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In preferred embodiments, the compositions are prepared in a form adapted for intranasal administration, i.e., for administration via the nasal mucosa. In one embodiment, the composition is a nasal preparation. Nasal preparations suitable for use in the present invention include, but are not limited to, nasal drops, nasal spray, gel, ointment, cream, lotion, skin patch, powder or suspension, administered using a dispenser or other device as needed. A variety of dispensers and delivery vehicles are known in the art, including single-dose ampoules, atomizers, nebulizers, pumps, nasal pads, nasal sponges, nasal capsules, and the like.

In certain embodiments, the nasal preparation can be a solid, semi-solid, or liquid form. In the case of a solid form, the components may be mixed together by blending, tumble mixing, freeze-drying, solvent evaporation, co-grinding, spray-drying, and other techniques known in the art.

In one embodiment, the composition is formulated in a semi-solid preparation suitable for intranasal administration, such as an aqueous or oil-based gel or ointment. For example, the active ingredients can be mixed with microspheres of starch, gelatin, collagen, dextran, polylactide, polyglycolide or other similar materials that are capable of forming hydrophilic gels. The microspheres can be loaded with drug, and upon administration form a gel that adheres to the nasal mucosa.

In one embodiment, the nasal preparation is in liquid form, which can include an aqueous solution, an aqueous suspension, an oil solution, an oil suspension, or an emulsion, depending on the physicochemical properties of the composition components. The liquid preparation is administered as a nasal spray or as nasal drops, using devices known in the art, including nebulizers capable of delivering selected volumes of formulations as liquid-droplet aerosols. For example, a commercially available spray pump with a delivery volume of 50 or 100 μL is available from, for example, Valois (Congers, N.Y.) with spray tips in adult size and pediatric size.

In certain preferred embodiments, the compositions are prepared in a form adapted for pulmonary administration. For instance, the liquid pharmaceutical composition may be lyophilized prior to use in pulmonary delivery, where the lyophilized composition is milled to obtain the finely divided dry powder consisting of particles within a desired size range noted above. For another instance, spray-drying may be used to obtain a dry powder form of the liquid pharmaceutical composition, and the process is carried out under conditions that result in a substantially amorphous finely-divided dry powder consisting of particles within the desired size range. For methods of preparing dry powder forms of pharmaceutical compositions, see, for example, WO 96/32149; WO 97/41833; WO 98/29096; and U.S. Pat. Nos. 5,976,574; 5,985,248; 6,001,336; and 6,875,749 herein incorporated by reference. In addition, the dry powder form of the pharmaceutical composition may be prepared and dispensed as an aqueous or nonaqueous solution or suspension, in a metered-dose inhaler.

In addition, a pharmaceutically effective amount of the dry powder form of the composition may be formulated as an aerosol or other preparation suitable for pulmonary inhalation. The amount of dry powder form of the composition placed within the delivery device is sufficient to allow for delivery of a pharmaceutically effective amount of the composition to the subject by inhalation. The delivery device delivers, in a single or multiple fractional doses, by inhalation, a pharmaceutically effective amount of the composition to the subject.

When used in the context of pharmaceutical compositions suitable for intranasal and pulmonary delivery, these terms have the following intended meaning. By "aqueous" is intended a composition prepared with, containing, or dissolved in water, including mixtures wherein water is the predominating substance in the mixture. By "nonaqueous" is intended a composition prepared with, containing, or dissolved in a substance other than water or mixtures wherein water is not the predominating substance in the mixture. By "solution" is intended a homogeneous preparation of two or more substances, which may be solids, liquids, gases, or intercombinations thereof. By "suspension" is intended a mixture of substances such that one or more insoluble substances are homogeneously dispersed in another predominating substance.

For purposes of the present invention, the terms "solid" and "dry powder" are used interchangeably with reference to the pharmaceutical compositions. By "solid" or "dry powder" form of a pharmaceutical composition is intended the composition has been dried to a finely-divided powder having moisture content below about 10% by weight, usually below about 5% by weight, and preferably below about 3% by weight. This dry powder form of the composition consists of particles comprising the peptides of the subject invention. Preferred particle sizes are less than about 90.0 μm mean diameter, more preferably less than about 70.0 μm, more preferably less than about 50.0 μm even more preferably about less than about 30.0 μm, more preferably less than about 10.0 μm, more preferably less than about 7.0 μm, even more preferably in the range of 0.1 to 5.0 μm, most preferably in the range of about 1.0 to about 5.0 μm diameter.

A surfactant may be added to the pharmaceutical composition to reduce adhesion of the dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a composition as a nonaqueous suspension are commercially available. Examples of such devices include the Ventolin metered-dose inhaler (Glaxo Inc., Research Triangle Park, N.C.) and the Intal Inhaler (Fisons, Corp., Bedford, Mass.). See also the aerosol delivery devices described in U.S. Pat. Nos. 5,522,378; 5,775,320; 5,934,272; and 5,960,792 herein incorporated by reference.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, vol. 2, pp. 115-138 (1984).

The compositions of the present invention can be provided in a form suitable for delivery by inhalation. Devices and formulations suitable for delivery by inhalation are known to the skilled person. The composition may be prepared for delivery as an aerosol in a liquid propellant, for example for use in a pressurised metered dose inhaler (PMDI's). Propellants suitable for use in a PMDI are known to the skilled person, and include CFC-12, HFA-134a, HFA-227, HCFC-22 (difluorochloromethane), HFA-152 (difluoroethane and isobutane).

In one embodiment, the present invention is formulated for topical administration, for treatment of CF-related skin diseases. Suitable topical formulations include, but are not limited to, lotion, gel, ointment, cream, and skin patch formulations.

The therapeutic or pharmaceutical compositions of the invention can be formulated as neutral or salt forms. Pharmaceutically acceptable salts include those formed with hydrochloric, phosphoric, acetic, oxalic, tartaric acids; sodium, potassium, ammonium, calcium, zinc, copper, and ferric hydroxides.

In one embodiment, the invention also provides a pharmaceutical pack or kit comprising one or more containers filled with one or more of the ingredients, e.g., compound, carrier, of the pharmaceutical compositions of the invention.

In one embodiment, the present invention provides a kit comprising the composition of the present invention; and optionally, a container, a label, an instruction, and, optionally, a delivery device for inhalation (such as an inhaler, propellants).

In another embodiment, the present invention provides a kit comprising a container containing the active ingredients of the present invention; and optionally, 1) one or more containers comprising water, therapeutically acceptable carriers, excipients, buffering agents, dispersing agents, bulking agents, surfactants, diluents, colorants, and/or preservatives; and 2) a label, an instruction, and, optionally, a delivery device for inhalation (such as an inhaler, propellants).

In one embodiment, the label indicates that the composition is used for treating cystic fibrosis and/or diseases induced by cystic fibrosis (e.g., lung diseases induced by cystic fibrosis). In another embodiment, the instruction provides procedures for administration of the composition for treatment of cystic fibrosis and/or diseases induced by cystic fibrosis (e.g., lung diseases induced by cystic fibrosis).

Routes of Administration

The compositions of the present invention can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection. In preferred embodiments, the composition is administered via intranasal, pulmonary, or oral route.

In preferred embodiments, the compositions of the present invention are administered in any route suitable for intranasal and/or pulmonary delivery. For purposes of the present invention, pharmaceutical compositions can be administered via inhalation of an aerosol or other suitable preparation that is obtained from an aqueous or nonaqueous solution or suspension form, or a solid or dry powder form of the pharmaceutical composition, depending upon the delivery device used.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. Such a unit dose may be administered more than once a day, e.g., two or three times a day.

The amount of active ingredient that may be combined with the carrier materials to produce a single dos-age form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Materials and Methods

Animal Preparation

Normally fed, 8-week-old, male NIH Swiss mice are sacrificed by $CO_2$ inhalation, followed by cervical dislocation. The small intestine is gently removed, and the segment is washed and flushed in ice-cold Ringer's solution. Then the mucosa is separated from the serosa and the muscular layers by stripping through the submucosal plane as previously described (Zhang et al. (2007) *J Physiol* 581(3):1221-1233). Following exsanguinations, ileal mucosa is obtained from a 10 cm segment close to the caecum. All experiments are approved by the University of Florida Institutional Animal Care and Use Committee.

Bio-Electric Measurements

Ion transport studies are performed on ileal sheets. Tissues are then mounted in between the two halves of an Ussing type-Lucite chamber with 0.3 $cm^2$ exposed surface areas (P2304, Physiologic Instruments, San Diego, Calif., USA). Regular Ringer's solution (115 mM NaCl, 25 mM $NaHCO_3$, 4.8 mM $K_2HPO_4$, 2.4 mM $KH_2PO_4$, 1.2 mM $MgCl_2$ and 1.2 mM $CaCl_2$) bubbled with 95% $O_2$: 5% $CO_2$ is used bilaterally as bathing solution for the tissues and the temperature is maintained constant at 37° C. The chambers are balanced to eliminate osmotic and hydrostatic forces. Resistance due to fluid is also compensated. The tissues are allowed to stabilize. The basal short-circuit current ($I_{sc}$) and the corresponding conductance (G) are recorded using a computer controlled voltage/current clamp device (VCC MC-8, Physiologic Instruments).

Flux Studies

Isotope of Sodium, $^{22}Na$, is used to study Na flux across the mucosa under basal conditions followed by addition of glucose. Conductance-paired tissues are designated to study serosal to mucosal flux ($J_{sm}$) representing secretory function, and mucosal to serosal flux ($J_{ms}$) representing absorptive function. $^{22}Na$ is added in to the designated side of the tissue and 500 μl samples are collected every 15 minutes from the other side. In a separate set of tissues $^{36}Cl$ is added to either the serosal or the mucosal side. Glucose of 8 mM concentration is added into the chamber for full stimulation, and the corresponding changes in $I_{sc}$ and conductance are recorded. Conductance is recorded based on the Ohm's law.

Three samples are collected under each condition. Radioactvity is counted using gamma counter. Tissues with conductance less than 10% change are matched and the average $J_{net}=J_{ms}-J_{sm}$ is calculated.

Protein Kinase A (PKA) Inhibitor Studies

Tissues paired with similar conductance and current are treated with or without 100 μM H-89 (Santa Cruz Biotechnology, Inc, Santa Cruz, Calif.), an irreversible protein kinase A (PKA) inhibitor. The tissues are incubated with H-89 for 30 minutes. Increasing concentrations of glucose (0.015-8 mM) are added every 5 minutes and the peak current is noted. Saturation kinetic constant is calculated for the corresponding $K_m$ and $V_{max}$ for treated and untreated tissues.

Caco-2 Cell Culture

Caco-2 cells differentiate post-confluence into cells with functional characteristics of fetal ileal epithelium. Caco-2 cells produce microvilli and have increased expression of small intestine specific transport proteins including SGLT1 and are therefore widely used as a model system for studying enterocyte function.

Caco-2 cells are obtained from ATTC and cultured in Dulbecoo's modified Eagle's medium supplemented with 10% fetal calf serum (FCS) and 1% nonessential amino acids at 37° C. and 5% $CO_2$. Caco-2 cells are passaged for 20-25 times and are seeded ($2\times10^5$ cells/dish) on 5 cm petri-dishes and grown until 80% confluence, when the FCS concentration is changed to 5%. Cells are grown for another 10 days before they are used for functional studies.

Confocal $Ca^{2+}$ Fluorescence Microscopy

Caco2 cells grown in 25 mm round coverslips are mounted on the bath chamber RC-21BR attached to series 20 stage adapter (Warner Instruments, CT USA). The cells are maintained at 37° C. using a single channel table top heater controller (TC-324B, Warner Instruments, CT USA). Cells are loaded with the fluorescent calcium indicator Fluo-8 AM dye (Cat #0203, TEFLab, Inc., Austin, Tex. USA) at 0.5 μM concentration at room temperature and incubated for 45 minutes. Confocal laser scanning microscopy is performed using an inverted Fluoview 1000 IX81 microscope (Olympus, Tokyo, Japan) and a U Plan S-Apo 20× objective. Fluorescence is recorded by argon lasers with excitation at 488 nm and emission at 515 nm. The Fluorescent images are collected with scanning confocal microscope. Solutions of either Ringer, glucose-containing Ringer's or BAPTA-AM-containing glucose-Ringer's solution are added to the bath using a multi-valve perfusion system (VC-8, Warner instruments, Hamden Conn., USA) controlled using a VC-8 valve controller (Warner instruments, Hamden Conn., USA). Changes are recorded and fluorescence is measured for various cells. Cells are washed with Ringer's solution and the experiment is repeated with the use of 3-O-methylglucose and carbechol (positive control).

Colorimetric cAMP Measurements

Freshly isolated mucosal scrapings of ileal epithelial cells are washed three times in Ringer's solution containing 1.2 mM $Ca^{2+}$ at 37° C. Washed cells are then divided into two groups and treated with either saline or 6 mM glucose and incubated for 45 minutes. Cells are treated with 0.1 M HCl to stop endogenous phosphodiesterase activity. The lysates are then used for cAMP assay using cAMP direct immunoassay kit (Calbiochem, USA).

The quantitative assay of cAMP uses a polyclonal antibody to cAMP that binds to cAMP in samples in a competitive manner. After a simultaneous incubation at room temperature, the excess reagents are washed away and substrates are added. After a short incubation time, the reaction is stopped and the yellow color generated is read at 405 nm. The intensity of the color is inversely proportional to the concentration of cAMP in standards and samples. cAMP levels are standardized to protein levels from respective fractions and expressed in pmol (mg protein)$^{-1}$.

Forskolin treated cells are used as a positive control. Glucose and forskolin treated cells are incubated for 45 minutes. All the assays are performed in triplicate and repeated until n=4 different mice.

EXAMPLES

Following are examples which illustrate procedures and embodiments for practicing the invention. This example should not be construed as limiting. All percentages are by weight and all solvent mixture proportions are by volume unless otherwise noted.

Figure 2:
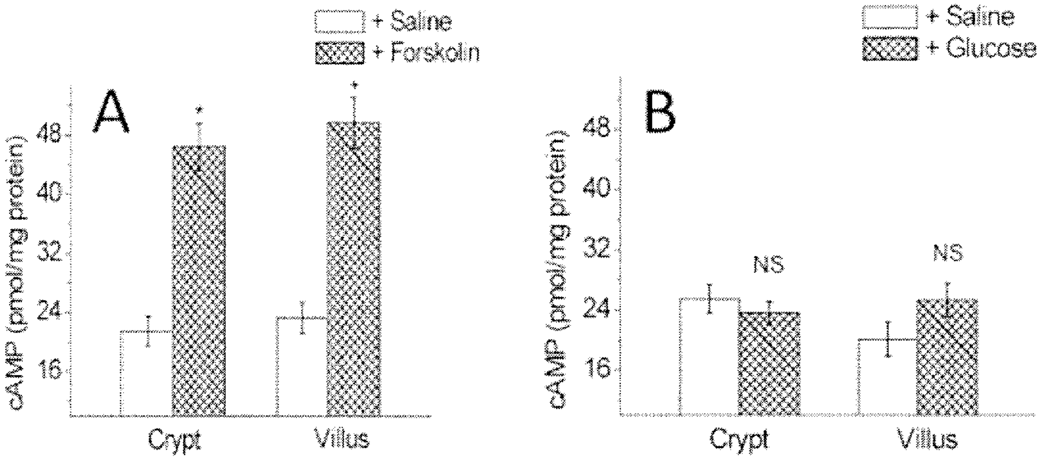
FIG. 2 shows effect of glucose and 3-O-methyl-glucose on intracellular cAMP in villus and crypt cells from ileum. Forskolin treatment significantly increases intracellular cAMP levels in crypt and villus cells (A). Incubating the cells with 8 mM glucose does not result in any significant change in the intracellular cAMP levels in both the crypt cells and villus cells (B). Columns represent the mean values and bars show the S.E.M. The values are from n=4 different mice repeated in triplicate. cAMP levels are standardized to protein levels from respective fractions and expressed as pmol·(mg protein)$^{-1}$. * P<0.001 compared with group after addition of forskolin. NS=not significant between saline treated and glucose treated villus cells (Bonferroni's multiple comparisons).
Figure 3:
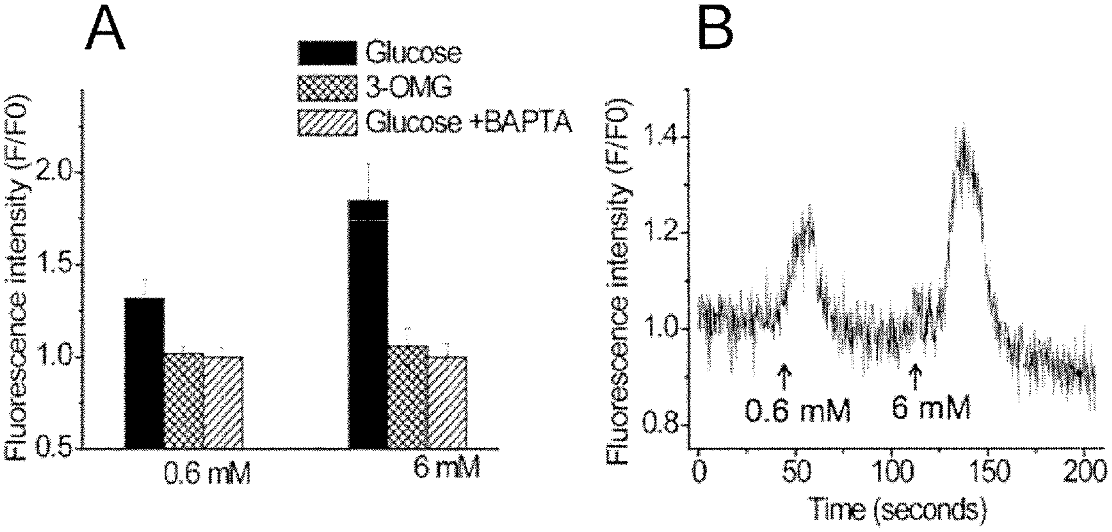
FIG. 3 shows the effect of glucose and 3-O-methyl-glucose on intracellular $Ca^{2+}$ in Caco-2 cells. (A) 0.6 mM glucose results in significant increase in fluorescence. 6 mM glucose results in significant increase in fluorescence compared to control and 0.6 mM. Pre-incubating the cells (45 minutes) with BAPTA fails to show a glucose-stimulated increase in intracellular $Ca^{2+}$. 3-OMG results in little increase in glucose-stimulated intracellular $Ca^{2+}$ compared to similar concentration of glucose. (B) shows representative trace to show 0.6 and 6 mM glucose-stimulated increase in intracellular $Ca^{2+}$.
Figure 4:
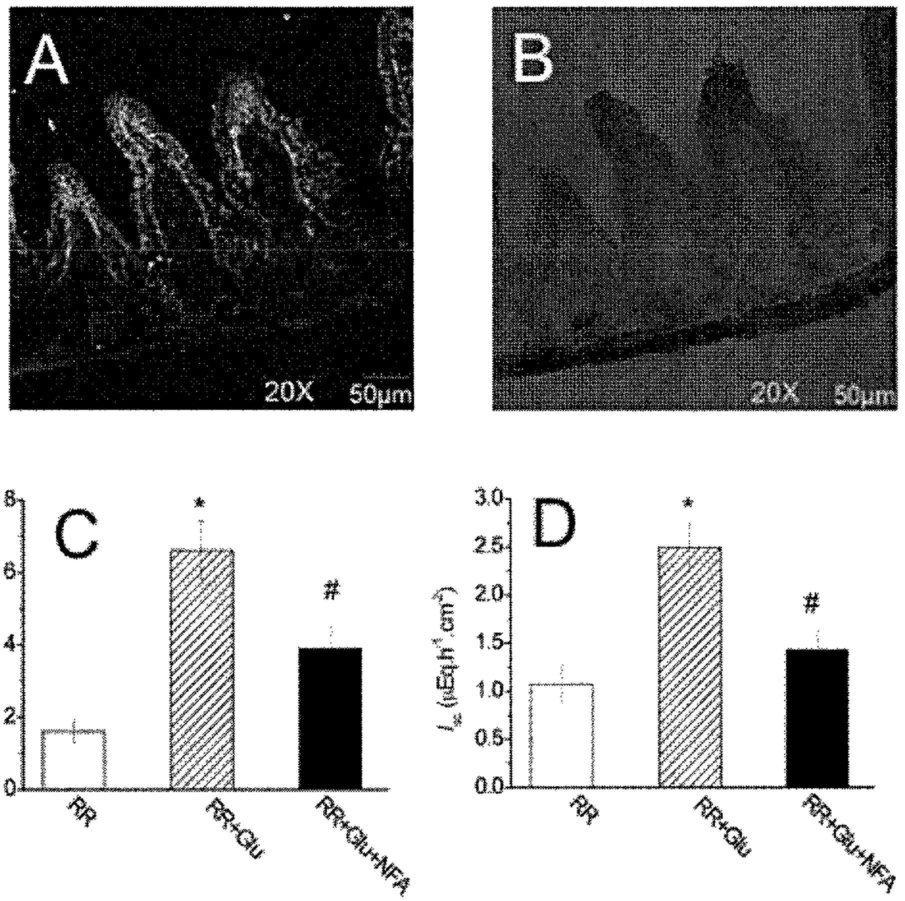
FIG. 4 shows immunohistochemistry studies that show that sodium-coupled glucose transport occurs in villus cells (A & B) and Ussing chamber studies that show glucose-stimulated increase in $I_{sc}$ is partially inhibited by niflumic acid (NFA) in ileal mucosa (C) and Caco-2 cells (D). For immunohistochemistry studies, 6 mM thickness frozen sections from mouse ileum are stained using Alexa Fluor 488 conjugated goat anti-rabbit IgG. Sections are viewed under laser scanning confocal microscope using 488 nm laser and 20× Objective. (A) SGLT1 expression occurs mostly in the villus cell region (B) shows corresponding white field image. (C) Addition of 8 mM glucose to the lumen side of ileal tissues mounted in Ussing chamber results in significant increase in $I_{sc}$. Addition of niflumic acid (NFA) 100 μM to the lumen side results in partial inhibition of the glucose-stimulated increase in $I_{sc}$. Similarly, addition of NFA to the apical side of Caco-2 cells grown on permeable inserts (0.4 μM) results in significant inhibition of glucose-stimulated increase in $I_{sc}$.*, $p<0.001$, compared with basal group after addition of glucose. #, $p<0.01$ compared with glucose group after addition of NFA.
Figure 5:
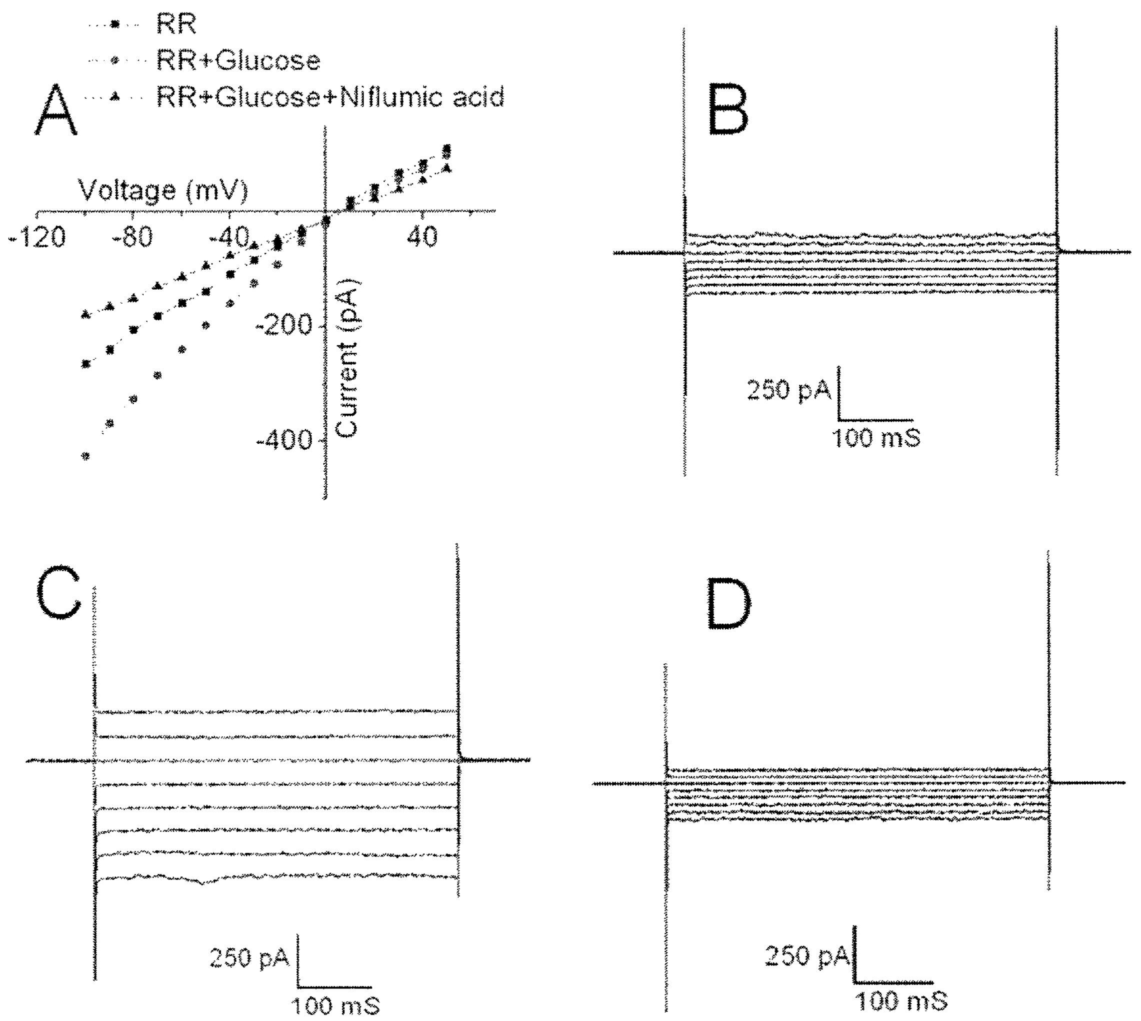
FIG. 5 shows gramicidin perforated whole cell currents in Caco-2 cells. (A) shows a family of superimposed current-voltage (I-V) relationship. In the presence of regular Ringer, the trace shows a weakly rectifying inward current (-■-). Addition of glucose results in a significant increase in the inward current (-●-). Calcium-activated $Cl^-$ channel blocker, niflumic acid (100 mM), added in the continued presence of glucose inhibits the glucose activated inward current (-◀-). (B) shows representative current in regular Ringer. (C) shows representative current after incubating the cells in 6 mM glucose for 5 minutes. (D) shows representative current in the presence of glucose and subsequent addition of niflumic acid and waiting for 5 minutes. Alternate traces at each holding potential have been removed to produce better clarity.

Example 1—Induction of Ion and Fluid Secretion by Glucose and Non-Metabolizable Glucose Analog This Example shows that glucose and non-metabolizable glucose analogs induce secretion of chloride and other ions. FIG. 1 shows that $Cl^-$ secretion contributes to the net glucose-stimulated increase in $I_{sc}$. FIG. 2 shows effect of glucose and 3-O-methyl-glucose on intracellular cAMP in villus and crypt cells from ileum. FIG. 3 shows the effect of glucose and 3-O-methyl-glucose on intracellular $Ca^{2+}$ in Caco-2 cells. FIG. 4 shows that sodium-coupled glucose transport occurs in villus cells (A & B) and glucose-stimulated increase in $I_{sc}$ is partially inhibited by niflumic acid (NFA) in ileal mucosa (C) and Caco-2 cells (D). FIG. 5 shows that glucose results in a significant increase in chloride secretion in Caco-2 cells.

Example 2—Induction of Ion Secretion in Cells Via the Co-Administration of a Substrate for Sodium-Glucose Transporter (SGLT-1) and NSP4

This Example shows that the co-administration of a substrate for sodium-glucose transporter (SGLT-1) and a NSP4 protein, NSP4 peptide, or NSP4 toxoid potently induces ion secretion.

Figure 6:
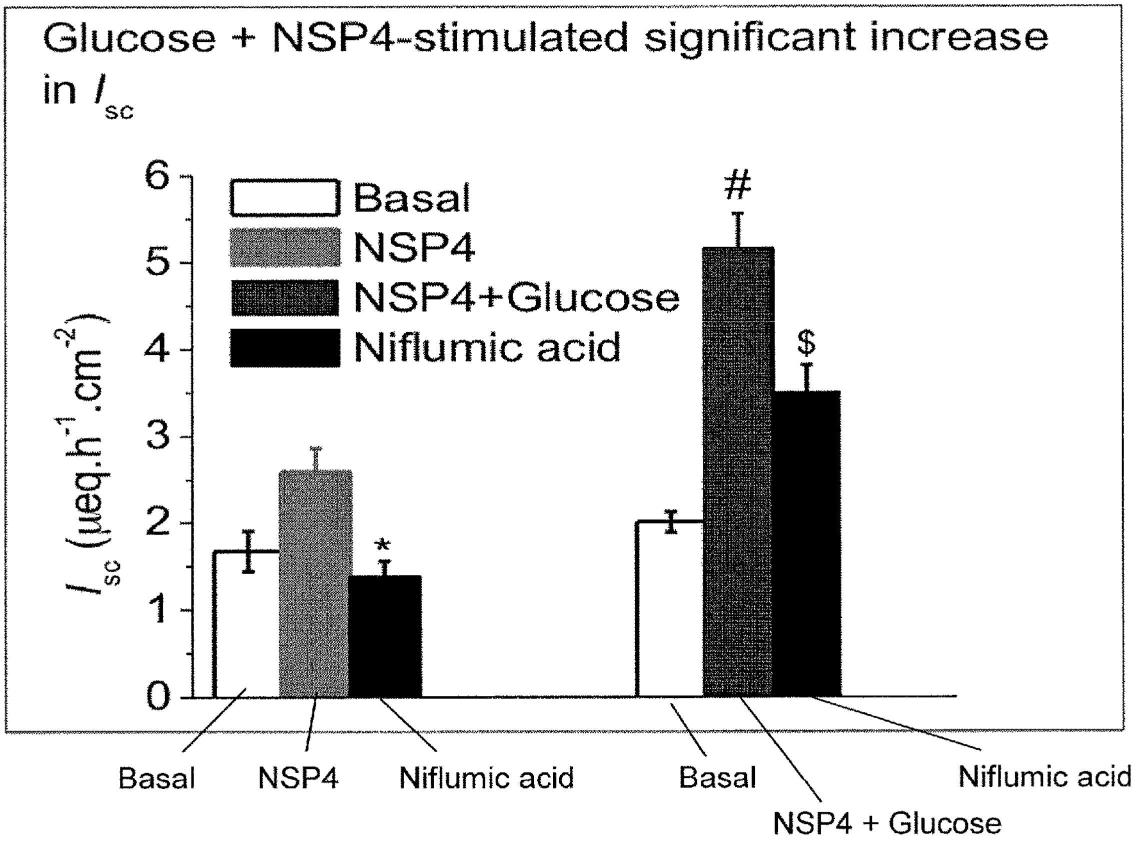
FIG. 6 shows that glucose and NSP4, when administered together, stimulate significant increase in Isc. Niflumic acid (NFA) (100 μM) abolishes $NSP4_{114-135}$ (SEQ ID NO:5)-stimulated current. NFA-sensitive current in the presence of NSP4 and glucose is four times higher than the NFA-sensitive current in the presence of NSP4 alone.

The results, as shown in FIG. 6, show that the combination of a NSP4 peptide and glucose increases anion secretion. Also, the increase in anion secretion induced by the combination of a NSP4 peptide and glucose is not completely inhibited by niflumic acid (NFA). The results indicate that the combination of a NSP4 peptide and glucose activates anion secretion via NFA-sensitive and NFA-insensitive mechanisms.

Figure 7:
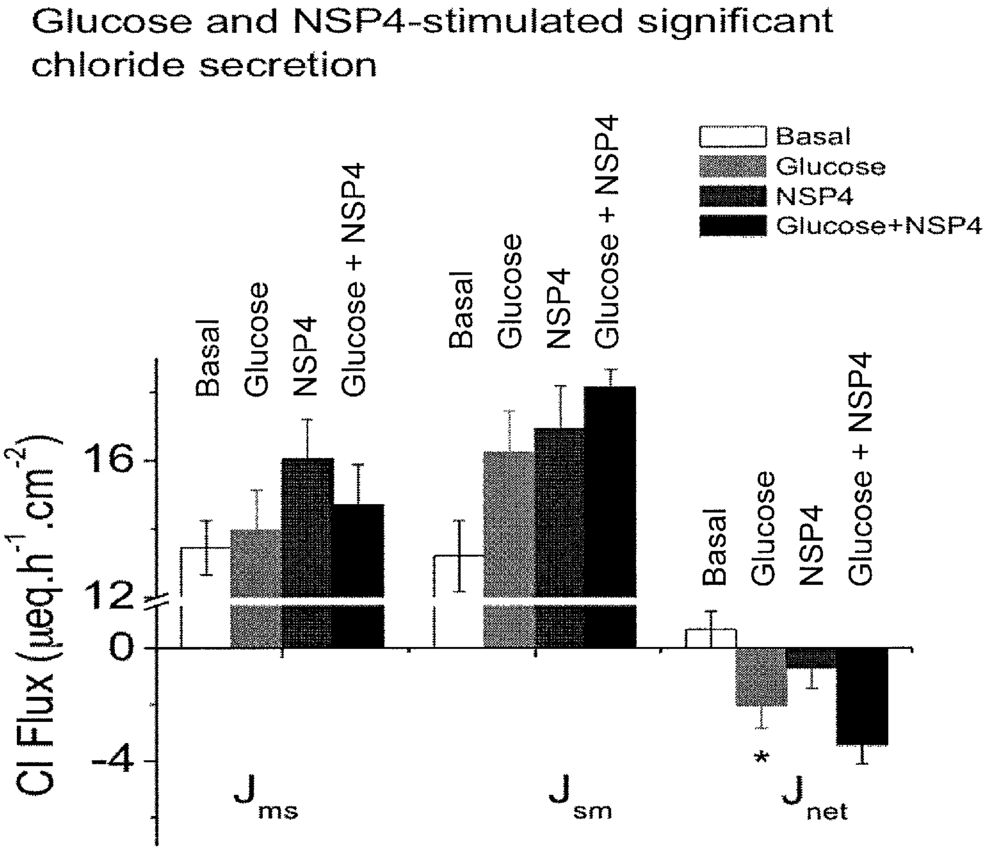
FIG. 7 shows that glucose and NSP4, when administered together, stimulate significant chloride secretion.

The results, as shown in FIG. 7, show that the combination of a NSP4 peptide and glucose enhances net chloride secretion. Also, the increase in chloride secretion induced by the combination of a NSP4 peptide and glucose is not completely inhibited by niflumic acid (NFA). The results indicate that the combination of a NSP4 peptide and glucose activates chloride secretion via NFA-sensitive and NFA-insensitive mechanisms.

Figure 8:
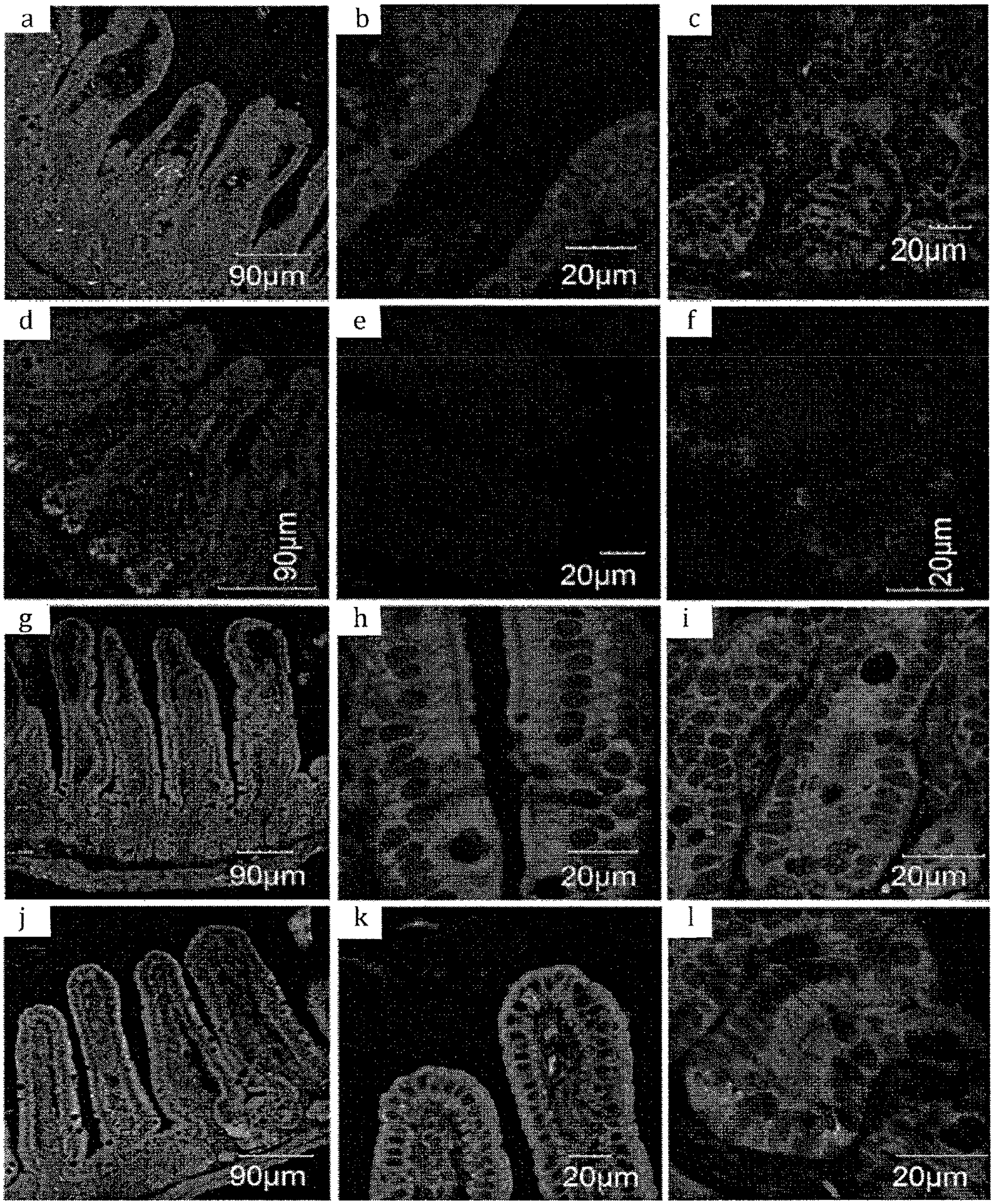
FIG. 8 shows tissues incubated in the presence of Ringer's solution (a, b, c), NSP4 (d, e, f), 8 mM glucose (g, h, i), NSP4+ glucose (j, k, l). Tissues incubated with NSP4+ glucose (j, k, l) show a higher level of expression for anoctamin 1 (ANO1) than tissues incubated with Ringer's solution (a, b, c), NSP4 (d, e, f), and glucose (g, h, i).

FIG. 8 shows that tissues incubated with NSP4 and glucose (j, k, l) show a higher level of expression for ANO1 chloride channel protein than tissues incubated with Ringer's solution (a, b, c), NSP4 (d, e, f), and glucose (g, h, i).

Figure 9:
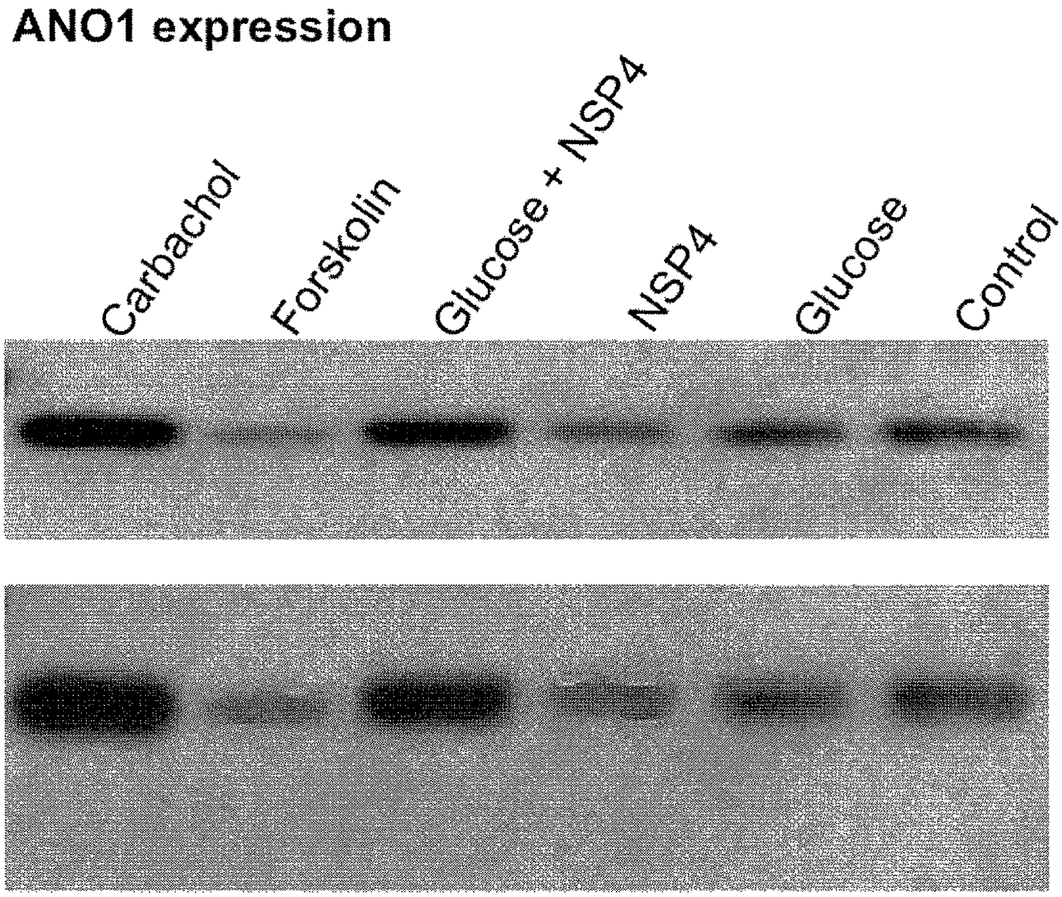
FIG. 9 shows Western blot results that show that tissues incubated with glucose and NSP4 have increased anoctamin 1 (ANO1) protein levels.

The immunohistochemistry data, as shown in FIG. 9, shows that tissues incubated with glucose and NSP4 have increased expression of anoctamin 1 (ANO1)—a calcium-activated chloride channel.

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

We claim:

1. A pharmaceutical composition comprising glucose and a pharmaceutically acceptable carrier, wherein the glucose is present at a concentration of about 0.3 mM to about 3.0 mM, wherein the composition further comprises a NSP4 protein comprising SEQ ID NO: 5; and wherein said NSP4 protein is present at a concentration of about 2.0 µM to about 12 µM.

2. The pharmaceutical composition of claim 1, formulated for intranasal or pulmonary delivery.

3. The pharmaceutical composition of claim 1, formulated as an aerosol.

4. The pharmaceutical composition of claim 1, formulated as a nasal spray.

5. The pharmaceutical composition of claim 1, wherein the pH is about 7.1 to about 7.5.

6. The pharmaceutical composition of claim 1, wherein said NSP4 protein consists of SEQ ID NO: 5.

7. A method for treating cystic fibrosis comprising administering, to a subject in need of such treatment, an effective amount of a composition of claim 1.

8. The method of claim 7, wherein the composition is administered via intranasal or pulmonary delivery.

* * * * *

UNITED STATES PATENT AND TRADEMARK OFFICE

CERTIFICATE OF CORRECTION

PATENT NO. : 10,086,007 B2
APPLICATION NO. : 14/390301
DATED : October 2, 2018
INVENTOR(S) : Sadasivan Vidyasagar et al.

It is certified that error appears in the above-identified patent and that said Letters Patent is hereby corrected as shown below:

In the Specification

Column 5,
Line 47, "CF-containing" should read -- $Cl^-$-containing --.
Line 48, "CF free" should read -- $Cl^-$ free --.

Column 10,
Lines 15-16, "acid or vitamins" should read -- and/or vitamins --.

Column 17,
Line 19, "single dos-age" should read -- single dosage --.

Signed and Sealed this
Twenty-ninth Day of January, 2019

Andrei Iancu
*Director of the United States Patent and Trademark Office*

SEQUENCE LISTING

<160> NUMBER OF SEQ ID NOS: 5

<210> SEQ ID NO 1
<211> LENGTH: 175
<212> TYPE: PRT
<213> ORGANISM: Human rotavirus A

<400> SEQUENCE: 1

```
Met Glu Lys Phe Thr Asp Leu Asn Tyr Thr Leu Ser Val Ile Thr Leu
1               5                   10                  15

Met Asn Ser Thr Leu His Thr Ile Leu Glu Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Val Lys Tyr Cys Ile Val Thr Ile Leu Asn Thr Leu Leu
65                  70                  75                  80

Lys Leu Ala Gly Tyr Lys Glu Gln Ile Thr Thr Lys Asp Glu Ile Glu
                85                  90                  95

Lys Gln Met Asp Arg Val Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Arg Ile Tyr Asp Lys Leu Ile Val Arg Ser Thr Asp Glu Ile Asp Met
    130                 135                 140

Thr Lys Glu Ile Asn Gln Lys Asn Val Arg Thr Leu Glu Glu Trp Glu
145                 150                 155                 160

Asn Gly Lys Asn Pro Tyr Glu Pro Lys Glu Val Thr Ala Ala Met
                165                 170                 175
```

<210> SEQ ID NO 2
<211> LENGTH: 175
<212> TYPE: PRT
<213> ORGANISM: Simian rotavirus A/SA11

<400> SEQUENCE: 2

```
Met Glu Lys Leu Thr Asp Leu Asn Tyr Thr Leu Ser Val Ile Thr Leu
1               5                   10                  15

Met Asn Asn Thr Leu His Thr Ile Leu Glu Asp Pro Gly Met Ala Tyr
            20                  25                  30

Phe Pro Tyr Ile Ala Ser Val Leu Thr Val Leu Phe Ala Leu His Lys
        35                  40                  45

Ala Ser Ile Pro Thr Met Lys Ile Ala Leu Lys Thr Ser Lys Cys Ser
    50                  55                  60

Tyr Lys Val Val Lys Tyr Cys Ile Val Thr Ile Phe Asn Thr Leu Leu
65                  70                  75                  80

Lys Leu Ala Gly Tyr Lys Glu Gln Ile Thr Thr Lys Asp Glu Ile Glu
                85                  90                  95

Lys Gln Met Asp Arg Val Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Arg Ile Tyr Asp Lys Leu Thr Val Gln Thr Thr Gly Glu Ile Asp Met
    130                 135                 140
```

```
Thr Lys Glu Ile Asn Gln Lys Asn Val Arg Thr Leu Glu Glu Trp Glu
145                 150                 155                 160

Ser Gly Lys Asn Pro Tyr Glu Pro Arg Glu Val Thr Ala Ala Met
                165                 170                 175


<210> SEQ ID NO 3
<211> LENGTH: 175
<212> TYPE: PRT
<213> ORGANISM: murine rotavirus

<400> SEQUENCE: 3

Met Glu Lys Leu Ala Asp Leu Asn Tyr Thr Leu Gly Val Ile Thr Leu
1               5                   10                  15

Met Asn Asp Thr Leu His Asn Ile Leu Glu Glu Pro Gly Met Val Tyr
            20                  25                  30

Phe Pro Tyr Ile Ala Ser Ala Leu Thr Val Leu Phe Thr Met His Lys
        35                  40                  45

Ala Ser Leu Pro Ala Met Lys Leu Ala Met Arg Thr Ser Gln Cys Ser
    50                  55                  60

Tyr Arg Ile Ile Lys Arg Val Val Val Thr Leu Val Asn Thr Leu Leu
65                  70                  75                  80

Arg Leu Gly Gly Tyr Asn Asp Tyr Leu Thr Asp Lys Asp Glu Thr Glu
                85                  90                  95

Lys Gln Ile Asn Arg Val Val Lys Glu Leu Arg Gln Gln Leu Ala Met
            100                 105                 110

Ile Glu Lys Leu Thr Thr Arg Glu Ile Glu Gln Val Glu Leu Leu Lys
        115                 120                 125

Arg Ile Tyr Asp Met Met Val Val Cys Arg Asp Arg Glu Ile Asp Met
    130                 135                 140

Ser Lys Glu Thr Asn Arg Lys Ala Phe Lys Thr Leu His Asp Trp Gly
145                 150                 155                 160

Ser Asp Arg Asn Tyr Asp Asp Asn Thr Asp Val Ile Ala Pro Leu
                165                 170                 175


<210> SEQ ID NO 4
<211> LENGTH: 175
<212> TYPE: PRT
<213> ORGANISM: Porcine rotavirus A

<400> SEQUENCE: 4

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Met Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Ile Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125
```

-continued

```
Arg Ile His Asp Lys Leu Ala Ala Arg Ser Val Asp Ala Ile Asp Met
    130                 135                 140

Ser Lys Glu Phe Asn Gln Lys Asn Ile Arg Thr Leu Asp Glu Trp Glu
145                 150                 155                 160

Ser Gly Lys Asn Pro Tyr Glu Pro Ser Glu Val Thr Ala Ser Met
                165                 170                 175


<210> SEQ ID NO 5
<211> LENGTH: 22
<212> TYPE: PRT
<213> ORGANISM: Artificial sequence
<220> FEATURE:
<223> OTHER INFORMATION: NSP4 114-135 peptide

<400> SEQUENCE: 5

Asp Lys Leu Thr Thr Arg Glu Ile Glu Gln Val Glu Leu Leu Lys Arg
1               5                   10                  15

Ile Tyr Asp Lys Leu Thr
            20
```